United States Patent [19]

Frey et al.

[11] Patent Number: 4,908,033
[45] Date of Patent: Mar. 13, 1990

[54] HIP JOINT ACETABULUM

[75] Inventors: Otto Frey, Winterthur; Rudolf Koch, Berlingen, both of Switzerland

[73] Assignee: Sulzer Brothers Limited, Winterthur, Switzerland

[21] Appl. No.: 204,108

[22] Filed: Jun. 8, 1988

[30] Foreign Application Priority Data

Jul. 9, 1987 [CH] Switzerland ........................ 2607/87

[51] Int. Cl.$^4$ .............................................. A61F 2/34
[52] U.S. Cl. ..................................................... 623/22
[58] Field of Search ....................... 623/16, 18, 19, 20, 623/22, 23; 403/135, 122, 125

[56] References Cited

U.S. PATENT DOCUMENTS

| Re. 28,895 | 7/1976 | Noiles | 623/22 |
|---|---|---|---|
| 3,806,960 | 4/1974 | Weber | 623/22 |
| 4,365,358 | 12/1982 | Judet | 623/22 |
| 4,408,360 | 10/1983 | Keller | 623/23 |
| 4,624,674 | 11/1986 | Pappas et al. | 623/22 |

FOREIGN PATENT DOCUMENTS

| 0066092 | 12/1982 | European Pat. Off. | 623/22 |
|---|---|---|---|
| 3602081 | 10/1986 | Fed. Rep. of Germany | 623/22 |
| 2300542 | 9/1976 | France | 623/23 |
| 2519248 | 7/1983 | France | 623/22 |
| 1573608 | 8/1980 | United Kingdom | 623/23 |

Primary Examiner—Richard J. Apley
Assistant Examiner—David J. Isabella
Attorney, Agent, or Firm—Kenyon & Kenyon

[57] ABSTRACT

The hip joint acetabulum uses a synthetic ring for snap-fitting the acetabulum body within the outer bowl. The ring is slit to provide for the snap fit connection and is provided with an annular lug which projects into an annular groove within the outer bowl. Recesses are also provided to permit a tool to penetrate into the acetabulum to separate the lug from the remainder of the ring to permit ready detachment of the body from the bowl.

17 Claims, 1 Drawing Sheet

HIP JOINT ACETABULUM

This invention relates to a hip joint acetabulum.

As is known, various types of hip joint acetabulae have been known. However, the materials which optimally fulfill the diverse demands placed on a hip joint acetabulum are not known at this time. Therefore, in order to obtain optimum conditions, for example, for body compatibility on the one hand and good tribologic response on the other hand, one is forced to use an outer bowl and an acetabular body of different materials. In many cases, the outer bowl has been made of titanium or a titanium alloy while the acetabular body is made of a CoCrMo cast alloy. However, in such cases, a problem is encountered as to how to connect the outer bowl and the acetabular body in a simple manner with each other so that they are immovable relative to each other while at the same time being detachable.

Published European Patent Application No. 0066092 describes a hip joint acetabulum of multi-component structure wherein an outer bowl and an acetabular body are connected together by means of a spline type connection. However, in this case, the components cannot be readily detached to permit removal of the body.

German OS No. 3602081 describes a hip joint acetabulum which utilizes a split ring to connect an acetabular body to an outer bowl. However, the split ring has been encased within the body so that detachment of the acetabular body from the bowl cannot be readily accomplished.

Accordingly, it is an object of the invention to connect the outer bowl and acetabular body of a multi-component hip joint acetabulum in an immobile manner while at the same time permitting ready detachability of the components.

It is another object of the invention to provide a relatively simple hip joint acetabulum which can be constructed of snap-fitted parts and which can be readily separated into the component parts.

Briefly, the invention provides a hip joint acetabulum which is comprised of an outer bowl of non-deformable material having an inwardly directly annular groove and an acetabular body of non-deformable material disposed within the bowl with a cavity for receiving a joint head of a femur prosthesis and an Outwardly directed annular groove. In accordance with the invention, a split ring of synthetic material is disposed in the groove of the body and is provided with an annular lug which projects radially outwardly into the groove of the bowl to detachably secure the body to the bowl. In addition, the bowl is provided with a plurality of recesses in an equatorial surface which are disposed in communication with the groove in the bowl in order to accommodate a tool for detaching the lug from the remainder of the ring in order to permit removal of the body from the bowl when desired.

The construction of the acetabulum is such that the bowl and body may be made of different materials. For example, the bowl may be made of a metal selected from the group consisting of titanium and titanium alloy while the body is made of a CoCrMo cast alloy.

The acetabulum is also provided with a means for preventing relative twisting between the bowl and the body. In addition, the bowl is provided with a pair of cylindrical surfaces s for receiving the body in sliding relation. The cylindrical surfaces are disposed to guide the body prior to engagement of the lug of the synthetic ring in the groove of the bowl.

The elasticity of the synthetic material ring permits the snap fit closure of the acetabular body within the outer bowl, particularly where the body and bowl are made of non-deformable, that is, non-elastic materials.

These and other objects and advantages of the invention will become more apparent from the following detailed description taken in conjunction with the accompanying drawings wherein.

Figure 1:
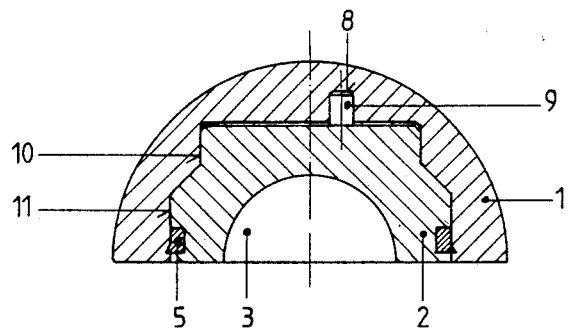
FIG. 1 illustrates a cross sectional view of a hip joint acetabulum constructed in accordance with the invention.

Referring to FIG. 1, the hip joint acetabulum is comprised of an outer bowl 1 of non-deformable or non-elastic material, such as a metal selected from the group consisting of titanium and titanium alloy since the bowl is to be in contact with body tissue over a relatively large area. In addition, an acetabular body 2 of non-deformable material is disposed within, the bowl 1 and is provided with a cavity or acetabular bowl 3 for receiving a joint head (not shown) of a femur prosthesis. Since the material of the body 2 requires good tribologic properties, the body 2 is made, for example of a CoCrMo cast alloy of known composition.

Figure 2:
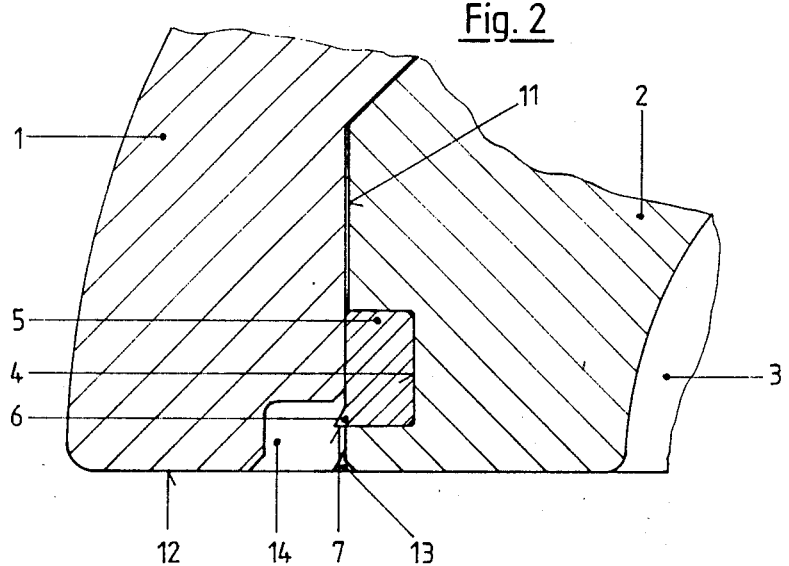
FIG. 2 illustrates an enlarged detail view of the snap-fit connection between the body and bowl of the acetabulum in accordance with the invention.
Figure 3:
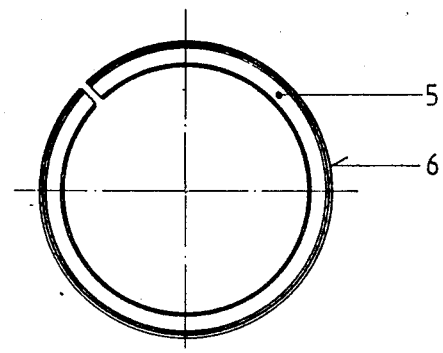
FIG. 3 illustrates a plan view of the synthetic split ring in accordance with the invention.

Referring to FIG. 2, the acetabular body 2 is provided with an outwardly directed annular groove 4 near the equatorial surface 12 into which a ring 5 of synthetic material is placed. As indicated in FIG. 3, the ring 5 is split at one location along the circumference.

The ring 5 also has an annular lug 6 projecting radially outwardly into an inwardly directed annular groove or depression 7 in the outer bowl 1. The snap-fit arrangement of the lug 6 in the annular groove 7 ensures a firm but detachable connection of the body 2 and the bowl 1.

Referring to FIG. 1, a means is provided for preventing relative twisting between the bowl 1 and the body 2. As indicated, this means includes a recess 8 in the bowl 1 and a pin 9 on the body 2 which is received within the recess 8. As indicated, the recess 8 is positioned in an eccentric position relative to the central axis of the acetabulum. Preferably, the pin 9 fits with a snug fit within the recess 8.

In order to facilitate mounting of the body 2 within the bowl 1, the bowl 1 is provided with a pair of coaxially disposed cylindrical surfaces 1 , 11 which are spaced apart on the interior so as to receive the body 2 in sliding relation. These cylindrical surfaces 10, 11 are disposed to guide the body 2 into the bowl 1 prior to engagement of the annular lug 6 of the ring 5 in the annular groove 7 of the bowl 2. That is, the cylindrical surfaces 10, 11 guide the body 2 during insertion before the ring 5 establishes contact with the equatorial surface 12 of the outer bowl. As indicated in FIG. 2, the bowl 1 is provided with a chamfer 13 at the inner edge for easier "threading-in" of the acetabular body 2.

Referring to FIG. 2, the bowl 1 is provided with a plurality of diametrically opposed recesses 14, only one of s which is shown, within the equatorial surface 12. Each recess 14 is also in communication with the annular groove 7 of the bowl 1. For example, the recesses 14 are sized to accommodate a tool (not shown) for detaching the lug 6 from the remainder of the ring 5 in order to permit removal of the body 2 from the bowl. In this respect, the tool is able to reach behind the lug 6 so as to shear the lug 6 from the remainder of the ring 5. Once the lug 6 is separated, the body 2 may be removed from the bowl 1. When implanting the body again, a new ring 5 is placed in the groove 4 before the body 2 is slid into the bowl 1.

The invention thus provides a hip joint acetabulum which can be formed of materials which meet the optimum requirements of the acetabulum and wherein the components of the acetabulum can be readily snap-fitted together in a firm connection. In addition, the connection is such that the connection may be broken at an appropriate time for removal of the acetabular body from the outer bowl. This may occur, for example, when the acetabular body has been worn by a femur prosthesis to a point at which the body must be replaced.

What is claimed is:

1. A hip joint acetabulum comprising
   an outer bowl of non-deformable material having an inwardly directed annular groove;
   an acetabular body of non-deformable material disposed within said bowl, said body having a cavity for receiving a joint head of a femur prosthesis and an outwardly directed annular groove;
   a split ring of synthetic material disposed in said groove of said body and having an annular lug projecting radially outwardly from a minor circumferential periphery of said ring into said groove of said bowl to secure said body to said bowl, said lug being detachable from the remained of said ring to permit removal of said body from said bowl.

2. A hip joint acetabulum as set forth in claim 1 wherein said ring by shearing is elastic.

3. A hip joint acetabulum as set forth in claim 1 wherein said bowl is made of a different material from said body.

4. A hip joint acetabulum as set forth in claim 1 wherein said bowl is made of a metal selected from the group consisting of titanium and titanium alloy and said body is made of a CoCrMo cast alloy.

5. A hip joint acetabulum as set forth in claim 1 which further comprises means for preventing relative twisting between said bowl and said body.

6. A hip joint acetabulum as set forth in claim 5 wherein said means includes a pin on one of said bowl and said body and a recess on the other of said bowl and said body receiving said pin.

7. A hip joint acetabulum as set forth in claim 1 wherein said bowl has a pair of cylindrical surfaces therein receiving said body in sliding relation.

8. A hip joint acetabulum as set forth in claim 7 wherein said cylindrical surfaces are coaxially disposed in spaced relation to guide said body therein prior to engagement of said lug in said groove of said bowl.

9. A hip joint acetabulum as set forth in claim 1 wherein said bowl has a plurality of recesses in an equatorial surface thereof and in communication with said groove in said bowl to accommodate a tool for shearing said lug from said ring to permit removal of said body from said bowl.

10. A hip joint acetabulum comprising
    an outer bowl of a metal selected from the group consisting of titanium and titanium alloy and having an inwardly directed annular groove;
    an acetabular body of non-deformable material disposed within said bowl, said body having a cavity for receiving a joint head of a femur prosthesis and an outwardly directed annular groove; and
    a split ring of synthetic material disposed in said groove of said body and having an annular lug projection radially outwardly from a minor circumferential periphery of said ring into said groove of said bowl to secure said body to said bowl, said lug being detachable from the remainder of said ring to permit removal of said body from said bowl.

11. A hip joint acetabulum as set forth in claim 10 which further comprises means for preventing relative twisting between said bowl and said body.

12. A hip joint acetabulum as set forth in claim 10 wherein said bowl has a pair of cylindrical surfaces therein receiving said body in sliding relation.

13. A hip joint acetabulum as set forth in claim 12 wherein said cylindrical surfaces are coaxially disposed in space relation to guide said body therein prior to engagement of said lug in said groove of said bowl.

14. A hip joint acetabulum as set forth in claim 10 wherein said bowl has a plurality of recesses in an equatorial surface thereof and in communication with said groove in said bowl to accommodate a tool for shearing said lug from said ring to permit removal of said body from said bowl.

15. A hip joint acetabulum comprising
    an outer bowl of non-deformable material having an interior surface with an inwardly directed annular groove therein;
    an acetabular body of non-deformable material slidably disposed within said bowl on said surface, said body having a cavity for receiving a joint head of a femur prosthesis and an outwardly directed annular groove facing said interior surface and said groove of said bowl; and
    a split ring of synthetic material disposed in said groove of said body and slidably received on said surface of said bowl, said ring having an annular lug projecting radially outwardly from a minor circumferential periphery of said ring into said groove of said bowl to secure said body of said bowl, said lug being detachable from the remainder of said ring to permit removal of said body from said bowl.

16. A hip joint acetabulum as set forth in claim 15 wherein said surface is cylindrical.

17. A hip joint acetabulum as set forth in claim 15 wherein said bowl has a plurality of recesses in an equatorial surface thereof and in communication with said groove in said bowl to accommodate a tool for shearing said lug from said ring to permit removal of said body from said bowl.

* * * * *

UNITED STATES PATENT AND TRADEMARK OFFICE
CERTIFICATE OF CORRECTION

PATENT NO. : 4,908,033

DATED : March 13, 1990

INVENTOR(S) : OTTO FREY, et al

It is certified that error appears in the above-identified patent and that said Letters Patent is hereby corrected as shown below:

Column 1, line 47 "Outwardly" should be -outwardly-
Column 1, line 67 cancel "s"
Column 2, line 24 "acetabuIar" should be -acetabular-
Column 2, line 25 "within, the" should be -within the-
Column 2, line 52 "1 , 11" should be -10, 11-
Column 2, line 65 cancel "s"
Column 3, line 34 "remained" should be -remainder-
Column 3, line 35 "to permit" should be -by shearing to permit-
Column 3, line 50 "other of" should be -other side of-
Column 4, line 17 "ring to" should be -ring by shearing to-
Column 4, line 52 "ring to" should be -ring by shearing to- Signed and Sealed this Twenty-eighth Day of April, 1992

Attest:

HARRY F. MANBECK, JR.

Attesting Officer

Commissioner of Patents and Trademarks